United States Patent [19]
Fagan et al.

[11] Patent Number: 5,645,529
[45] Date of Patent: Jul. 8, 1997

[54] DEVICES FOR SELECTIVELY DIRECTING INFLATION DEVICES

[75] Inventors: John R. Fagan, Pepperell; Jeffrey M. Kling, Tewksbury; Michael D. Barbere, Dunstable, all of Mass.

[73] Assignee: C. R. Bard, Inc., Murray Hill, N.J.

[21] Appl. No.: 213,463

[22] Filed: Mar. 14, 1994

Related U.S. Application Data

[63] Continuation of Ser. No. 29,447, Mar. 11, 1993, abandoned.

[51] Int. Cl.$^6$ ............................................. A61M 29/00
[52] U.S. Cl. ............................................. 604/101; 606/194
[58] Field of Search ............................... 604/96, 101, 282, 604/49, 52, 53; 606/192, 194

[56] References Cited

U.S. PATENT DOCUMENTS

| | | | |
|---|---|---|---|
| 4,292,974 | 10/1981 | Fogarty. | |
| 4,403,612 | 9/1983 | Fogarty. | |
| 4,581,017 | 4/1986 | Sahota | 604/101 |
| 4,608,984 | 9/1986 | Fogarty. | |
| 4,665,604 | 5/1987 | Dubowik | 604/282 X |
| 4,762,129 | 8/1988 | Bonzel. | |
| 4,787,388 | 11/1988 | Hofmann | 606/194 |
| 4,878,495 | 11/1989 | Grayzel | 604/101 X |
| 4,941,877 | 7/1990 | Montano, Jr.. | |
| 4,983,165 | 1/1991 | Loiterman | 604/95 |
| 4,983,167 | 1/1991 | Sahota. | |
| 5,019,042 | 5/1991 | Sahota. | |
| 5,041,125 | 8/1991 | Montano, Jr.. | |
| 5,049,132 | 9/1991 | Shaffer et al.. | |
| 5,071,406 | 12/1991 | Jang | 604/96 |
| 5,102,416 | 4/1992 | Rock | 606/194 |
| 5,108,370 | 4/1992 | Walinsky. | |
| 5,295,995 | 3/1994 | Kleiman | 606/194 |
| 5,304,135 | 4/1994 | Shonk | 604/101 |
| 5,308,323 | 5/1994 | Sogawa et al. | 604/95 |
| 5,320,605 | 6/1994 | Sahota | 604/101 |
| 5,383,856 | 1/1995 | Bersin | 604/101 |
| 5,395,332 | 3/1995 | Ressemann et al.. | |
| 5,403,280 | 4/1995 | Wang | 604/96 |
| 5,413,557 | 5/1995 | Solar | 604/96 |
| 5,433,706 | 7/1995 | Abiuso | 604/96 |

FOREIGN PATENT DOCUMENTS 246 998   11/1987   European Pat. Off..

OTHER PUBLICATIONS

"Parallel Angioplasty Dilatation Catheter and Guide Wire: A New Technique for the Dilatation of Calcified Coronary Arteries", Yazdanfar, et al; Catherization and Cardiovascular Diagnosis 28:72–75, Wiley-Liss, Inc. 1993.

Primary Examiner—Corrine M. McDermott
Attorney, Agent, or Firm—Morgan & Finnegan, L.L.P.

[57] ABSTRACT

Devices have been made which are balloon catheters, preferably PTCA devices, and which are capable of selectively directing inflation forces against the thicker part of an eccentric arterial obstruction or an off-center plaque deposit. In a first embodiment, a balloon catheter is formed from at least two balloons positioned side-by-side to each other. One balloon is larger in diameter than the other balloon(s). The larger diameter balloon acts as a cushion to the thinner part of a lesion. The small balloon(s) focuses greater inflation force against the thicker part of the lesion. In a second embodiment, a unitary balloon catheter has a plurality of independently inflatable lobes. Inflation forces may be selectively directed depending on which lumen of the balloon catheter is pressurized. Additionally, different lumens can be used for other purposes including an auto-perfusion catheter and monorail applications. The new devices provide a method of opening a constricted region in the cardiovascular system of a patient.

5 Claims, 2 Drawing Sheets

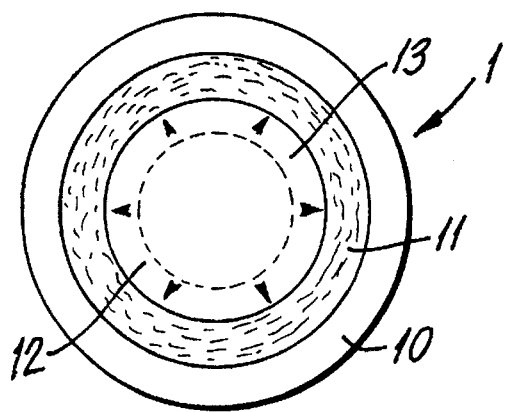
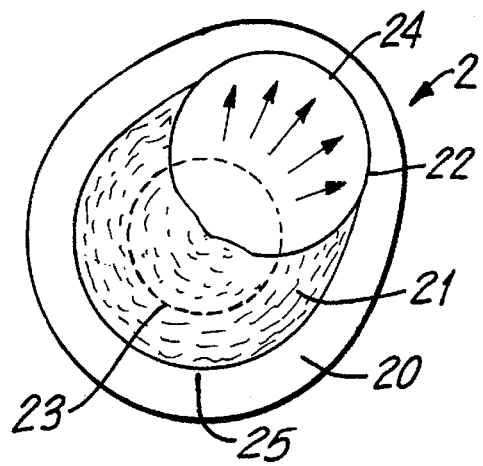
FIG. 1    FIG. 2
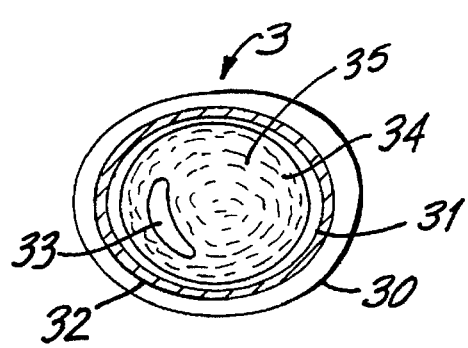
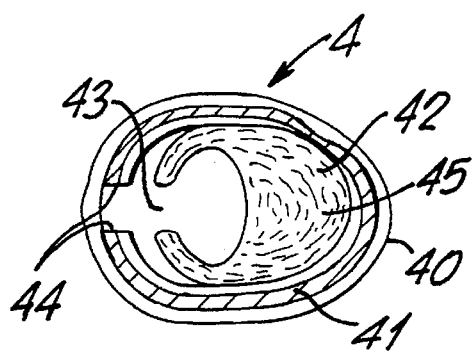
FIG. 3    FIG. 4
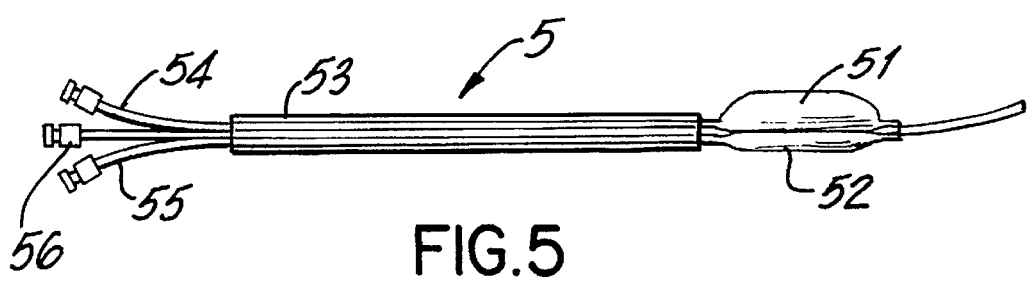
FIG. 5

DEVICES FOR SELECTIVELY DIRECTING INFLATION DEVICES

This is a continuation of application Ser. No. 08/029,447, filed on Mar. 11, 1993, now abandoned.

FIELD OF THE INVENTION

This invention relates to balloon catheters which are especially useful for opening a constricted region in the cardiovascular system of a patient in which the constricted region is non-concentric or eccentric relative to the diameter of the cardiovascular vessel.

BACKGROUND OF THE INVENTION

Coronary angioplasty has emerged as a viable present alternative to bypass surgery for revascularization of stenotic and occluded coronary arteries. Percutaneous coronary angioplasty is less invasive and less traumatic to the patient and is less expensive since the angioplasty patient will have a shorter hospital stay and a shorter post-procedure recovery time.

Percutaneous transluminal angioplasty is performed by use of a catheter which has a built-in inflatable and deflatable balloon. The balloon catheter can be passed through a guiding catheter and advanced inside a target artery toward the point of obstruction that needs to be dilated. When the balloon portion of the catheter is properly positioned inside the arterial obstruction, the balloon is inflated to a pressure sufficient to overcome the resistance of the arteriosclerotic plaque of the obstructed site. By inflating the balloon in the stenosis multiple times over a period of time, the desired dilation of the obstructed segment of the artery can be achieved.

The distribution of atherosclerotic plaque in coronary arteries can have two major types of cross-sectional luminal shapes, concentric and eccentric. If the plaque is distributed evenly along the entire circumference of the arterial internal elastic membrane, the coronary lumen is located centrally and is called a concentric type lesion. If the plaque does not involve the entire arterial circumference leaving a variable arc of disease-free wall (normal wall), the residual cross-sectional lumen is called eccentric. More often than not, the lumen through a stenosis is off center and rarely round. Recent studies have found that a high percentage of arterial lesions are eccentric.

Ischemic complications of percutaneous translumina coronary angioplasty (PTCA) occur in a significant number of patients and constitute a major cause of morbidity and mortality associated with PTCA. Variable degrees of intimal and media and plaque disruption occur during all PTCA procedures and may vary from mild superficial splitting to gross fissuring through the entire medial and plaque mass.

As noted above, coronary occlusions are not always concentric relative to the diameter of the artery and, in fact, most such lesions have been found to be eccentric. The use of PTCA in a patient with an eccentric stenosis does not necessarily move the bulk of the stenotic material out of the arterial lumen. Very often, the thinner side of the lesion gives way and the artery wall gives way with it. Media layer tear or dissection is common. Although lumenal space is increased thereby increasing blood flow by the lesion, extensive damage may be done to the arterial wall. This damage is well documented in the following references:

"The Eccentric Coronary Atherosclerotic Plaque: Morphologic Observations and Clinical Relevance". B. F. Waller, M.D. *Clinical Cardiology* 12, 14–20 (1989)

"Morphologic Correlate of Coronary Angiographics Patterns at the Site of PTCA". B. F. Waller, M.C. *Clinical Cardiology* 11,817–822 (1988)

"Morphology of Coronary Lesions in the Prediction of Early PTCA Outcome". Haft et al, *Catherization and Cardiovascular Diagnosis* 17: 69–74 (1989)

"Tear or Dissection After Coronary Angioplasty". King et al, *Circulation—Volume* 79, May 1989 pp. 1035–1041

"Vessel Plaque and Lumen Morphology After Transluminal Balloon Angioplasty". Lyon et at, *Arteriosclerosis*, Vol. 7, No. 3, May/June 1987

"Stress Analysis of the Diseased Arterial Cross Section". Vito, Whang, Giddens, Zadns, Glagov 1990. *Advances in Bioengineering ASME, BED—Vol.* 17

Very often balloon dilatation results in a situation where media and intima split along with the thin section of the stenosis. Because of material property (mechanical) differences within the stenotic material (it is not homogenous) and between the artery walls and the stenosis, delamination of the stenosis can also occur.

Detection of non-concentric lesions is easily done by using orthogonal views of the same anatomical area. Some lesions may look very minor in one view, but, when the same lesion is viewed at a fight angle to the first view, it may then seem extremely restrictive. Orthogonal viewing of the coronary arteries is very common and a long standing practice.

The consequence to lesion dissection is flow disruption which may lead to thrombus formation and early re-occlusion. It was hoped that the LABA [Laser Assisted Balloon Angioplasty] device would mitigate this problem. However, restenosis rates were not improved by this device.

The prior art includes patents disclosing a plurality of balloons positioned on the distal end of a dilation catheter as well as patents disclosing a plurality of lumens (luminae) having an inflatable lobe in communication with a respective tureen.

U.S. Pat. No. 4,787,388 to Hofmann discloses a multi-lobed balloon catheter having three lobes (balloons) that are independently and selectively inflatable by air passing through respective lumens communicating with the lobes. The Hofmann patent specifically teaches, however, that it is preferable for the balloons to be inflated together, such as from a common source (Col. 2, lines 46–54). The three balloons of the Hofmann catheter are formed independent from each other and form a triangular configuration (FIG. 3B). Because the balloons are separate from each other, the area between the balloons form passages which allow fluid flow between the balloons, thus forming a perfusion catheter. The balloons are substantially equal in size and preferably inflated together.

U.S. Pat. No. 5,071,406 to Jang discloses a balloon dilatation catheter having two or more independently inflatable balloons (FIG. 7) positioned on opposite sides of a catheter shaft. The first balloon has a longer length than the second balloon. The balloons share some common walls, and form a catheter construction having three effective diameters.

The catheter in Jang is constructed so that multiple balloons are formed from a single, monolithic piece of polymer material. This construction provides a smooth transition from balloon to balloon on the outside of the catheter. The balloons are formed so that one balloon may be longer and larger than the other balloon. One balloon is inflated while the other is deflated and, later, the inflated balloon is deflated and the deflated balloon inflated. The respective size of the inflated balloons thus varies for use in several stenoses or multi vessels.

U.S. Pat. No. 4,083,369 to Sinnreich discloses a surgical device used in gynecology. The device includes an inflatable balloon element formed of a relatively thicker wall area and an opposing thinner wall area. When the device is inserted within a body cavity, such as a uterus, the thinner wall area is adapted for contacting the raw tissues within a body cavity while the thicker wall section faces toward the less sensitive tissues, such as the forward abdominal wall.

U.S. Pat. No. 5,102,416 to Rock discloses a catheter having three expandable chambers that are selectively pressurized to cause the chambers to distend asymmetrically about the catheter's axis so that the catheter can be easily directed within a patient's venal system. Later, the chambers are equally inflated to provide a balloon which is symmetrical for use during an angioplasty procedure.

Other patents to Jang besides the '406 patent mentioned above include U.S. Pat. Nos. 4,744,366; 4,763,654; 4,958, 634; and 4,990,139. These patents disclose concentrically arranged balloons, and balloons that are positioned proximal and distal to each other.

U.S. Pat. No. 5,108,370 to Walinsky discloses a perfusion balloon catheter in which the outer membrane forming the balloon is selectively connected to the inner tube of the catheter forming a perfusion tureen between a vascular wall and the outer membrane.

U.S. Pat. No. 5,000,734 to Boussignac et al discloses a probe having a bag element (balloon) with at least one perfusion conduit formed in the bag.

Other patents disclose multiple balloons, either positioned tandem to each other, or concentric to each other. Examples include U.S. Pat. Nos. 4,445,892; 4,778777; 4,748,981; 4,986,830; 4,994,033; 5,002,532; and 5,049,132.

Other patents disclose multiple lumen catheters such as U.S. Pat. Nos. 4,584,998 and 4,846,791.

There is a continuing need to provide safer and more efficient PCTA devices which can be used to help all patients including those having eccentric coronary occlusions.

It is an object of the present invention to provide unique PCTA devices which can focus the inflation energy of the balloon portion to a specific point on an arterial lesion.

It is further object of the present invention to provide the ability in a PCTA procedure to direct the dilating force(s) in desired direction(s).

It is a still further object of the present invention to provide a PCTA device which eliminates or minimizes the possible occurrence of arterial wall damage.

SUMMARY OF THE INVENTION

The present invention relates to devices which are balloon catheters, preferably PTCA devices, and which are capable of selectively directing inflation forces against the thicker part of an eccentric arterial obstruction or an off-center plaque deposit.

In a first embodiment of the present invention, a balloon catheter is formed from at least two balloons positioned side-by-side to each other. One balloon is larger in diameter than the other balloon(s). The larger diameter balloon acts as a cushion to the thinner part of a lesion. The smaller balloon(s) focuses greater inflation force against the thicker part of the lesion.

In a second embodiment of the present invention, a unitary balloon catheter has a plurality of independently inflatable lobes. Inflation forces may be selectively directed depending on which lumen of the balloon catheter is pressurized. Additionally, different lumens can be used for other purposes including an auto-perfusion catheter and monorail applications.

By using the devices of the present invention, inflation pressure from a balloon is focused on the "thick" part of the lesion and not on the "thin" part. Hence, the vessel wall adjacent to the thin section may not be as affected. This is done, for example, by using two balloons side by side in the lesion with differing diameters. If the larger diameter balloon is inflated at a low pressure adjacent to the thin part of the lesion cross section and a small diameter balloon is inflated to a higher pressure adjacent to the thicker part, the larger diameter balloon acts as a cushion against the thin part. The force of the larger balloon is spread over a larger area while the smaller balloon inflation force is focused on the fat part of the lesion. This results in a fracture through the thicker portion of the lesion.

In the first embodiment of the present invention, the device has at least three lumens. At least two of the lumens independently inflate the balloons and one can carry a guide wire. The shaft is made of a multi-lumen extrusion or of a variation of coaxial arranged tubes. Three smaller tubes are placed in a larger tube to contain them as one shaft. There may be advantages to free floating tubes within a larger tube in flexing around bends. A multi-lumen tube might not be as flexible because of its integral structure.

One of each of the inflation tubes terminates inside each balloon while the lumen for the guide wire passes between the balloons and ends distal to the distal extremity of the balloons. The distal portions of the balloons are bonded to the distal end of the guide wire lumen. In a multi-lumen design, the shaft ends at the proximal segment of the balloons and the lumens are separated to connect to each balloon. A tip section can also be added to extend past the balloons for the guide wire.

The second embodiment of the present invention comprises a unitary multi-lumen (multi-lobe) dilation balloon in which the lumens (lobes) can be inflated independently or simultaneously of each other. This dilation balloon inflates to a non-round configuration. Each of the multiple lumens will naturally inflate round while the combination of all the lumens will inflate to a non-round geometry or configuration as a function of the number of lumens (lobes). This design allows the use of high pressure as a result of small lumens and provides advantageous folding properties. Because of the ability to independently inflate the lumens (lobes), there is a consequent ability to direct the dilation forces in desired directions. The resultant non-round balloon of the present invention applies greater forces in a desired direction.

The present invention also comprises a novel method of opening a constricted region in the cardiovascular system of a patient comprises the use of the novel PTCA devices of the present invention.

BRIEF DESCRIPTION OF THE FIGURES

FIG. 1 shows a cross-section of a concentric stenosis and concentric stretching

FIG. 2 shows a cross-section of eccentric stenosis and dilation of disease free wall FIG. 3 shows a cross-section of typical non-concentric (eccentric) stenosis FIG. 4 shows a cross-section of a vessel after balloon dilation of an eccentric stenosis FIG. 5 is a side elevation of the present asymmetric balloon dilation catheter

DETAILED DESCRIPTION OF THE FIGURES

Figures 6A, 6B, 6C:
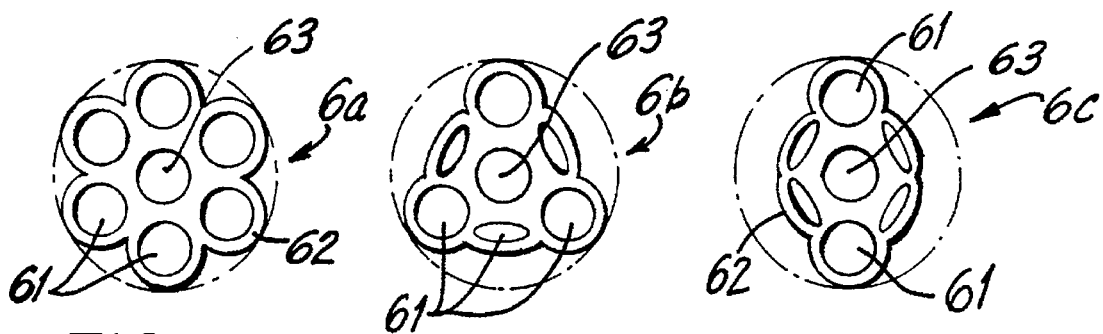
FIG. 6a, are cross-sectional views of embodiments of the present multi-lumen 6b, 6c (lobe) dilation balloon and 6d
Figure 6D:
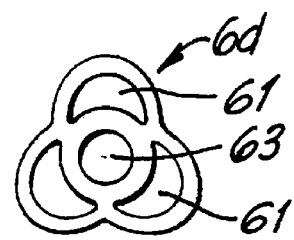

FIG. 1 shows a cross-sectional view of an obstructed artery 1. The arterial wall 10 encompasses a concentric stenosis of obstruction 11 within the arterial lumen 13. The figure shows a balloon 12 within the arterial lumen 13 which when inflated in the directions shown by the arrows compresses the stenosis or obstruction 11 as well as stretches the arterial wall 10. Because the stenosis or obstruction 11 is concentric with the arterial lumen 13, the inflated balloon is able to compress the stenosis or obstruction 11 in an even manner.

FIG. 2 shows a cross-sectional view of an obstructed artery 2 wherein the artery contains an eccentric (non-concentric) stenosis or obstruction 21. The normal arterial lumen as shown by the dotted lines 23 is partially blocked and the real arterial lumen actually present is shown at 22. The arterial wall at 24 is unobstructed. Because of the eccentric nature of the stenosis or obstruction, the arterial wall at 25 causes the stenosis or obstruction at 21.

FIG. 3 shows a cross-section of another possible type of eccentric or non-concentric stenosis or obstruction. In the figure, the obstructed artery 3 has an arterial wall 30 and lumina opening 33 is arc shaped because of the non-symmetric nature of stenosis or obstruction 34. Hence, if dilation is undertaken in such an obstruction with a prior art balloon catheter, intima 31 and media 32 will be subjected to uneven forces at one side of the artery as opposed to the side of the artery having the "fat" portion 35 of the stenosis or obstruction 34.

FIG. 4 shows a cross-section of an eccentric or non-concentric artery such as shown in FIG. 3 after balloon dilation with a prior art balloon catheter. The artery 4 of FIG. 4 has an arterial wall 40 with intima 41 and luminal opening after dilation 43. Because of the uneven force applied to the fat end 45 of stenosis or obstruction 42 during dilation, a site of dissection 44 has occurred.

FIG. 5 shows a catheter 5 according to the present invention which includes two dilatation balloons 51, 52 that are located side-by-side on the distal end of the catheter. One balloon 51 has a larger diameter than the other balloon 52. In accordance with the invention, during angioplasty, the smaller diameter balloon 52 is inflated to a higher pressure adjacent the thicker i.e., larger part of a lesion. The larger diameter balloon, which is inflated at a lower pressure than the smaller balloon, "cushions" the thinner i.e., smaller portion of the lesion and spreads the inflation force over a larger area while the inflation force of the smaller diameter balloon is focused against the thicker part of the lesion.

The catheter shaft 53 has three single lumens 54, 55, 56. Lumens 54, 55 inflate the balloons 51, 52 independently, and the third carries a guidewire. Preferably, the shaft comprises coaxially arranged, free-floating tubes to provide maximum flexibility. It is also preferable that the catheter outer jacket, which contains the three single lumen tubes, be made torqueable with the addition of a wire braid. This outer jacket may be constructed on a very thin wire in the order of 0.001 to 0.002 inches and embedded and encapsulated by a polymeric material such as polyamide, polyethlene terephthalate (PET), polyethylene and similar such polymeric materials. Preferably the braid wire is made of a high tensile material such as stainless steel. The braid may also be formed from a Kevlar thread.

Preferably the catheter shaft diameter is less than or equal to about 3.5 French (0.45") with a working length of about 135 cm. It is also preferable that the balloons are formed from a very strong material such as PET with a wall thickness of about 0.00025 inches to reduce the collapsible balloon in profile. The balloon diameters may range from about 1 mm to about 3 min.

FIGS. 6a, 6b, 6c, 6d and 7 show views of a multilobed balloon catheter in accordance with the present invention. The multilobed balloons of FIGS. 6a, 6b, 6c, 6d and 7 have any number of lumens 61 which can be inflated independently of each other or simultaneously and also has a shaft opening 63. The number of lumens inflated at one time is optional depending on the desired application. The overall shape of the balloon 6a, 6b, 6c, 6d or 7 is a function of the number of lumens (Lobes) or the number of inflated lumens (lobes) at any one time. Because of its configuration, this balloon catheter can focus the dilatation forces in desired directions as opposed to round balloons which apply forces equally in all directions. Also because of the small size of the lumens and corresponding smaller contact area of each lobe as compared with the larger contact area of a single large uniform round balloon the balloon catheter of the invention presents higher dilatation forces at each lobe than the single large balloon of the prior art.

In the PTCA device of the first embodiment of the invention, the balloons are not the same size, and are independently inflatable at different pressures, the smaller balloon being inflated at a higher pressure than the larger balloon. The present asymmetric balloon catheter also includes an outer jacket to hold the independent balloons (tubes) together.

It should be understood that while this first embodiment of the invention includes one large balloon and a smaller balloon those skilled in the art would readily understand that embodiments including one larger balloon and several smaller balloons are also encompassed within the scope of the present invention. It is clear that the larger balloon in any such embodiment functions as a cushion means to that portion of the diseased vessel which has a lesser degree or no degree of stenosis or obstruction.

Figure 7:
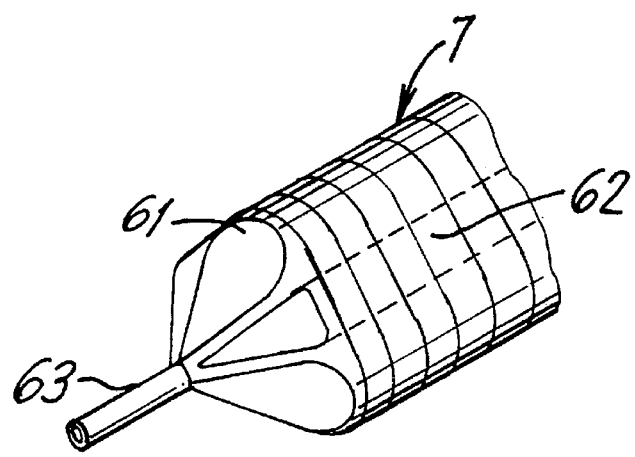
FIG. 7 is a side elevation showing an example of the present multi-lumen (lobe) balloon

In the other embodiment of the present invention, the multi-lumen, multi-lobed balloon catheter, has a plurality of independently inflatable lobes (balloons) forming different unique configurations, inflating to a non-round configuration. The overall balloon forms a unitary structure. Such balloons can be formed by using any known technique including, for example, blow molding. This balloon catheter provides effectively higher dilatation pressures at each lobe of higher pressure because of the smaller radius in each pressure component of the balloon, and also provides advantageous folding properties. Open tureens which are not being used to inflate lobes may be used to provide access for fluids or devices. For example, as shown in FIG. 7 some of the lumens 62 may be open from the proximal end of the balloon to the distal end thereof (not shown). These open lumens can be used to receive a guidewire which extends from the distal tip of the catheter, through the open balloon lumen and proximally exterior to the catheter shaft to the proximal end of the catheter. As such the catheter can be operated in a rapid exchange manner similar to that known in the art as discussed in U.S. Pat. No. B1 4,762,129 to Bonzel.

Alternatively, an open balloon lumen can be used to perfuse blood through the balloon while the balloon is inflated to minimize trauma that would be otherwise caused by the balloon fully occluding the artery when the balloon is inflated. With the present multi-lumen (Lobe) balloon catheter comes the ability to direct dilating forces in desired directions and without the need to position the balloon in order to direct the force. It is only required that the proper desired lumen(s) (Lobe(s)) be inflated. The present balloon allows the ability to have a balloon of a desired shape during dilation of a lesion and also allows the possibility of blood perfusion through the balloon. An additional advantage is the ability to pass a wire through the balloon for rapid exchange. It is believed that no other prior balloon can hold a shape at such high pressures as the present balloon nor does any prior balloon provide open lumens through which fluids or devices can pass during dilation of a lesion. The present balloon can be inflated into various shapes depending upon the number of lobes which are present. For example, if there are three lobes and all are inflated, the shape would be triangular. It is contemplated that the present balloon catheter can have at least two lumen (lobes), preferably 2 to 10 lumens (lobes). Additionally, the cross-sections shape of the unitary multi-lumen (lobe) balloon can have various configurations including, for example, substantially oval or substantially triangular. Illustrative such shapes are shown in FIGS. 6a, 6b, 6c and 6d.

The present invention also comprises a method for opening a constricted region in the cardiovascular system of a patient especially in those cases in which the lesion is non-concentric or eccentric. A balloon catheter is provided in which the balloon portion is capable of being inflated in such a manner that a higher dilation force (pressure) is exerted against a thicker (fat) portion of the constriction as opposed to the thinner portion of the constriction or non-diseased vessel. After the selective application of greater pressure to the fat portion of the obstruction, the balloon is contracted and withdrawn from the body of the patient.

When the balloon catheter of the first embodiment of the present invention is employed the balloon catheter is inserted into the cardiovascular system of the patient with the balloon in an unexpanded condition. After the balloon is within the obstructed region, the position of the catheter is adjusted such that the larger balloon is adjacent to the thin portion of the eccentric obstruction and the smaller balloon (or balloons) is adjacent the fat portion of the obstruction. The balloons are then inflated so as to perform dilation of the lesion, deflated and then withdrawn from the patient. Radiopaque markers can be provided on the balloon in order to guide the user in the proper placement of the balloon within the lesion.

When the balloon catheter of the second embodiment of the present invention is employed, the usual insertion is performed into the patient. However, since this embodiment provides for selective inflation, positioning may not be required. If desired, radiopaque markers can be present to allow for visualization during the procedure. After insertion and placement of the balloon at the lesion site, the lumen(s) (lobe(s)) of the balloon are selectively inflated in such a manner that a greater force (pressure) is exerted by the balloon against the fat portion of the lesion as compared to the thin lesion portion or non-diseased vessel wall. After dilation, the balloon lobes are contracted and the balloon catheter is withdrawn from the patient.

It should be understood, however, that the foregoing description of the present invention is intended merely to be illustrative thereof and that other embodiments and modifications may be apparent to those skilled in the art without departing from its spirit.

What is claimed:

1. A method for treating a constricted region in a blood vessel, said constricted region having first and second portions disposed in a plane orthogonal to the blood vessel, comprising the steps of:

inserting into the blood vessel a dilatation catheter having a dilatation element affixed thereto;

locating the dilatation element in said constricted region;

establishing contact between said dilatation element and said first and second portions of said constricted region; and applying a first, diffuse, cushioned dilatation force to said first contacted portion of said constricted region disposed in said plane and a second, focused, dilatation force to said second contacted portion of said constricted region disposed in said plane, said second dilatation force being higher than said first dilatation force.

2. A method for treating a constricted region in a blood vessel, the constricted region including first and second portions disposed in a plane orthogonal to the blood vessel, comprising the steps of:

inserting into the blood vessel a dilatation catheter having first and second dilatation balloon members disposed thereon, the dilatation balloon members being disposed eccentric to each other;

locating the dilatation balloon members in said plane;

inflating said balloon members so as to establish contact between said first and second dilatation balloon members and said first and second portions of said constricted region disposed in said plane, respectively, and so as to apply a first, diffuse, cushioned dilatation force to said first contacted portion of said constricted region disposed in said plane and a second, focused, dilatation force to said second contacted portion of said constricted region disposed in said plane, said second dilatation force being higher than said first dilatation force.

3. The method recited in claim 2 which further comprises the step of inflating each of said balloon members at a different pressure.

4. The method recited in claim 2 wherein said first balloon member is inflated with a lower pressure than that of the second balloon member.

5. A method for treating a constricted region in a blood vessel, the constricted region including a plane orthogonal to the blood vessel, the constricted region including first and second portions, the second portion having a greater degree of constriction than the first portion comprising the steps of:

inserting into the blood vessel a dilatation catheter having first and second dilatation balloon members disposed thereon, the dilatation balloon members being disposed eccentric to each other;

locating the dilatation balloon members in said plane, with said first dilatation balloon being disposed adjacent said first portion of the constricted region and the second dilatation balloon being disposed adjacent said second portion of the constricted region; and inflating said balloon members so as to establish contact between said first and second dilatation balloon members and respective first and second portions of said constricted region disposed in said plane and so as to apply a first, diffuse, cushioned dilatation force to said first contacted portion of said constricted region disposed in said plane and a second, focused, dilatation force to said second contacted portion of said constricted region disposed in said plane, said second dilatation force being higher than said first dilatation force.

* * * * *